United States Patent

Jelich et al.

Patent Number: 4,743,615
Date of Patent: May 10, 1988

[54] SUBSTITUTED PYRAZOLIN-5-ONES, COMPOSITION CONTAINING, AND METHOD OF USING THEM TO COMBAT FUNGI

[75] Inventors: Klaus Jelich, Wuppertal; Wilhelm Brandes, Leichlingen; Gerd Hänssler; Paul Reinecke, both of Leverkusen, all of Fed. Rep. of Germany

[73] Assignee: Bayer Aktiengesellschaft, Leverkusen, Fed. Rep. of Germany

[21] Appl. No.: 925,184

[22] Filed: Oct. 31, 1986

[30] Foreign Application Priority Data

Nov. 12, 1985 [DE] Fed. Rep. of Germany ....... 3539995

[51] Int. Cl.$^4$ .................... A01N 43/56; C07D 231/46
[52] U.S. Cl. ..................................... 514/404; 548/365
[58] Field of Search ......................... 548/365; 514/404

[56] References Cited

U.S. PATENT DOCUMENTS

| | | | |
|---|---|---|---|
| 2,510,696 | 6/1950 | Hunter et al. | 548/365 |
| 4,666,933 | 5/1987 | Jelich et al. | 548/365 |

FOREIGN PATENT DOCUMENTS

| | | | |
|---|---|---|---|
| 0166171 | 1/1986 | European Pat. Off. | 548/365 |
| 2434572 | 3/1980 | France | 564/45 |

*Primary Examiner*—Henry R. Jiles
*Assistant Examiner*—Kurt G. Briscoe
*Attorney, Agent, or Firm*—Sprung Horn Kramer & Woods

[57] ABSTRACT

Fungicidally active substituted pyrazolin-5-ones of the formula

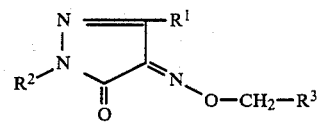

in which
$R^1$ and $R^2$ independently of one another each represents hydrogen, alkyl, alkenyl, alkinyl, cyanoalkyl, hydroxyalkyl, alkoxyalkyl, alkylthioalkyl, alkoxycarbonyl, hydroxycarbonylalkyl, alkoxycarbonylalkyl, aminocarbonylalkyl, alkylaminocarbonylalkyl or dialkylaminocarbonylalkyl, or represents in each case optionally substituted oxiranylalkyl, aralkyl, heterocyclyl or aryl, and
$R^3$ represents halogenoalkyl, halogenoalkenyl or halogenoalkinyl, or represents substituted cycloalkyl, or represents substituted cycloalkylalkyl.

17 Claims, No Drawings

SUBSTITUTED PYRAZOLIN-5-ONES, COMPOSITION CONTAINING, AND METHOD OF USING THEM TO COMBAT FUNGI

The invention relates to new substituted pyrazolin-5-ones, several processes for their preparation and their use as agents for combating pests.

It is already known that organic nitrogen compounds, such as, for example, zinc ethylene-1,2-bis-(dithiocarbamate) have fungicidal properties (compare, for example, R. Wegler "Chemie der Pflanzenschutz- und Schädlingsbekämpfungsmittel" ("Chemistry of Plant Protection Agents and Agents for Combating Pests"), Springer Verlag Berlin, Heidelberg, New York 1970, Volume 2, page 65 et seq.).

However, the action of these compounds is not always completely satisfactory in all fields of use, especially when low amounts and concentrations are applied.

New substituted pyrazolin-5-ones of the general formula (I)

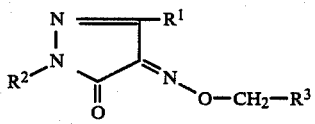

(I)

in which
R$^1$ and R$^2$ independently of one another each represent hydrogen, alkyl, alkenyl, alkinyl, cyanoalkyl, hydroxyalkyl, alkoxyalkyl, alkylthioalkyl, alkoxycarbonyl, hydroxycarbonylalkyl, alkoxycarbonylalkyl, aminocarbonylalkyl, alkylaminocarbonylalkyl or dialkylaminocarbonylalkyl, or represent in each case optionally substituted oxiranylalkyl, aralkyl, heterocyclyl or aryl and R$^3$ represents halogenoalkyl, halogenoalkenyl or halogenoalkinyl, or represents substituted cycloalkyl, or represents substituted cycloalkylalkyl,
have been found.

The compounds of the formula (I) can exist as geometric isomers or isomer mixtures of different composition. Both the pure isomers and the isomer mixtures are claimed according to the invention.

It has furthermore been found that the new substituted pyrazolin-5-ones of the general formula (I)

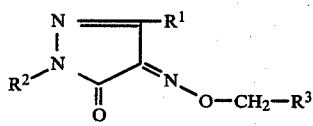

(I)

in which
R$^1$ and R$^2$ independently of one another each represent hydrogen, alkyl, alkenyl, alkinyl, cyanoalkyl, hydroxyalkyl, alkoxyalkyl, alkylthioalkyl, alkoxycarbonyl, hydroxycarbonylalkyl, alkoxycarbonylalkyl, aminocarbonylalkyl, alkylaminocarbonylalkyl or dialkylaminocarbonylalkyl, or represent in each case optionally substituted oxiranylalkyl, aralkyl, heterocyclyl or aryl and R$^3$ represents halogenoalkyl, halogenoalkenyl or halogenoalkinyl, or represents substituted cycloalkyl, or represents substituted cycloalkylalkyl, are obtained by a process in which
(a) 4-oximino-pyrazolin-5-ones of the formula (II)

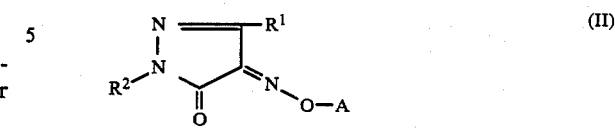

(II)

in which
R$^1$ and R$^2$ have the abovementioned meaning and
A represents hydrogen or an alkali metal cation,
are reacted with alkylating agents of the formula (III)

$$R^3-CH_2-X \qquad (III)$$

in which
R$^3$ has the abovementioned meaning and
X represents an electron-withdrawing leaving group,
if appropriate in the presence of a diluent, if appropriate in the presence of an acid-binding agent and if appropriate in the presence of a catalyst, or by a process in which
(b) alkoximinocarboxylic acid esters of the formula (IV)

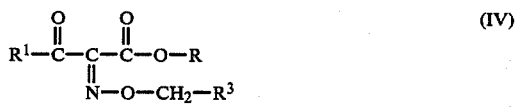

(IV)

in which
R represents alkyl and
R$^1$ and R$^3$ have the abovementioned meanings,
are reacted with hydrazine derivatives of the formula (V)

$$R^2-NH-NH_2 \qquad (V)$$

in which R$^2$ has the abovementioned meaning, if appropriate in the presence of a diluent, or by a process in which
(c) the 4-alkoxyimino-pyrazolin-5-ones obtainable by process (a) or by process (b), of the formula (Ia)

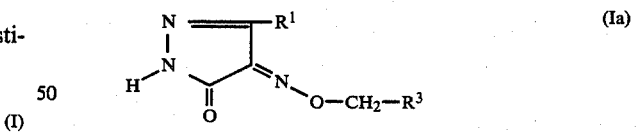

(Ia)

in which, R$^1$ and R$^3$ have the abovementioned meanings, are reacted with alkylating agents of the formula (VI)

$$R^{2'}-Y \qquad (VI)$$

in which
R$^{2'}$ represents alkyl, alkenyl, alkinyl, cyanoalkyl, hydroxyalkyl, alkoxyalkyl, alkylthioalkyl, hydroxycarbonylalkyl or alkoxycarbonylalkyl, or represents in each case optionally substituted aralkyl or heterocyclyl and
Y represents an electron-withdrawing leaving group, if appropriate in the presence of a diluent, if appropriate in the presence of an acid-binding agent and if appropriate in the presence of a catalyst.

Finally, it has been found that the new substituted pyrazolin-5-ones of the formula (I) can be used as agents for combating pests, above all as fungicides. Surprisingly, the new substituted pyrazolin-5-ones of the formula (I) exhibit better fungicidal properties than zinc ethylene-1,2-bis-dithiocarbamate, which is known from the prior art and is a closely related compound from the point of view of its action.

Alkyl in the definitions of $R^1$ and $R^2$ denotes straight-chain or branched alkyl with 1 to 8, preferably 1 to 4, carbon atoms. Methyl, ethyl, n-, i-propyl and n-, s-, t- and i-butyl may be mentioned.

Alkenyl in the definitions of $R^1$ and $R^2$ denotes alkenyl with up to 8, preferably up to 4, carbon atoms.

Cyanoalkyl in the definitions of $R^1$ and $R^2$ denotes cyanoalkyl with 1 to 8, in particular 1 or 2, carbon atoms in the alkyl part.

Hydroxyalkyl in the definitions of $R^1$ and $R^2$ denotes hydroxyalkyl with 1 to 8, in particular 1 or 2, carbon atoms in the alkyl part.

Alkoxyalkyl in the definitions of $R^1$ and $R^2$ denotes alkoxyalkyl with 1 to 8, in particular 1 or 2, carbon atoms per alkoxy or alkyl part.

Alkylthioalkyl in the definitions of $R^1$ and $R^2$ denotes alkylthioalkyl with 1 to 8, in particular 1 or 2, carbon atoms per alkylthio or alkyl part.

Alkoxycarbonyl in the definitions of $R^1$ and $R^2$ denotes alkoxycarbonyl with 1 to 8, in particular 1 or 2, carbon atoms in the alkoxy part.

Hydroxycarbonylalkyl in the definitions of $R^1$ and $R^2$ denotes a radical with 1 to 8, in particular 1 or 2, carbon atoms in the alkyl part.

Alkoxycarbonylalkyl in the definitions of $R^1$ and $R^2$ denotes a radical with 1 to 8, in particular 1 or 2, carbon atoms per alkoxy and alkyl radical.

Aminocarbonylalkyl in the definitions of $R^1$ and $R^2$ denotes a radical with 1 to 8, in particular 1 or 2, carbon atoms per alkyl part.

Mono- and dialkylaminocarbonylalkyl in the definitions of $R^1$ and $R^2$ denote a radical with 1 to 8, in particular 1 or 2, carbon atoms per alkyl radical.

Substituted oxiranylalkyl in the definitions of $R^1$ and $R^2$ denotes oxiranylalkyl which has 1 to 4, preferably 1 or 2, carbon atoms in the alkyl part and is optionally substituted by alkyl with 1 to 4, in particular 1 or 2, carbon atoms.

Aralkyl in the definitions of $R^1$ and $R^2$ denotes a radical with 6 to 10 carbon atoms, in particular 6, in the aryl part and 1 to 4 carbon atoms, in particular 1 or 2, carbon atoms, in the alkyl part.

Heterocyclyl in the definitions of $R^1$ and $R^2$ denotes a 5- or 6-membered ring with 1 to 3 identical or different hetero atoms, and oxygen, sulphur and nitrogen may be mentioned.

Aryl in the definitions of $R^1$ and $R^2$ denotes a radical with 6 to 10, in particular 6, carbon atoms.

Halogen as a substituent in the aryl radicals in the definitions of $R^1$ and $R^2$ denotes fluorine, chlorine, bromine and iodine, in particular fluorine, chlorine and bromine.

Alkyl as a substituent in the aryl radicals in the definitions of $R^1$ and $R^2$ denotes a straight-chain or branched radical with 1 to 4 carbon atoms.

Alkoxy as a substituent in the aryl radicals in the definitions of $R^1$ and $R^2$ denotes a radical with 1 to 4, in particular 1 or 2, carbon atoms.

Alkylthio as a substituent in the aryl radicals in the definitions of $R^1$ and $R^2$ denotes a radical with 1 to 4, in particular 1 or 2, carbon atoms.

Dioxyalkylene as a substituent in the aryl radicals in the definitions of $R^1$ and $R^2$ denotes a radical with 1 to 4, in particular 1 or 2, carbon atoms.

Alkylcarbonyloxy as a substituent in the aryl radicals in the definitions of $R^1$ and $R^2$ denoted a radical with 1 to 4, in particular 1 or 2, carbon atoms in the alkyl part.

Halogenoalkyl as a substituent in the aryl radicals in the definitions of $R^1$ and $R^2$ denotes a radical with 1 to 4, in particular 1, carbon atom and 1 to 9 identical or different halogen atoms, in particular chlorine and fluorine.

Halogenoalkoxy as a substituent in the aryl radicals in the definitions of $R^1$ and $R^2$ denotes a radical with 1 to 4, in particular 1, carbon atom and 1 to 9 identical or different halogen atoms, in particular fluorine.

Halogenoalkylthio as a substituent in the aryl radicals in the definitions of $R^1$ and $R^2$ denotes a radical with 1 to 4, in particular 1, carbon atom and 1 to identical or different halogen atoms, in particular fluorine.

Halogenoalkyl in the definition of $R^3$ denotes a radical with 1 to 12, in particular 1 to 8, carbon atoms and 1 to 8, in particular 1 to 5, identical or different halogen atoms.

Halogenoalkenyl in the definition of $R^3$ denotes a radical with 2 to 12, in particular 3 to 8, carbon atoms and 1 to 8, in particular 1 to 5, identical or different halogen atoms.

Halogenoalkinyl in the definition of $R^3$ denotes a radical with 2 to 12, in particular 3 to 8, carbon atoms and 1 to 8, in particular 1 to 5, identical or different halogen atoms.

Halogen in the halogenoalkyl, halogenoalkenyl and halogenoalkinyl definitions of $R^3$ denotes fluorine, chlorine, bromine and iodine, preferably fluorine, chlorine and bromine and in particular fluorine and chlorine.

Cycloalkyl in the definition of $R^3$ denotes a radical with 3 to 7, preferably 3 to 6 and in particular 3, carbon atoms.

Cycloalkylalkyl in the definition of $R^3$- denotes a radical with 3 to 7, preferably 3 to 6 and in particular 3, carbon atoms in the cycloalkyl part and 1 to 7, preferably 1 to 3 and in particular 1, carbon atom in the alkyl part.

Halogen as a substituent in the cycloalkyl parts in the definitions of $R^3$ denotes fluorine, chlorine, bromine or iodine, in particular fluorine or chlorine.

Alkyl as a substituent in the cycloalkyl parts in the definitions of $R^3$ denotes a straight-chain or branched radical with 1 to 4, in particular 1, carbon atom.

Halogenoalkyl as a substituent in the cycloalkyl parts in the definitions of $R^3$ denotes a radical with 1 to 4, in particular 1, carbon atom in the alkyl part and 1 to 9, in particular 3, halogen atoms, such as fluorine, chlorine, bromine and iodine, in particular fluorine.

Formula (I) provides a general definition of the substituted pyrazolin-5-ones according to the invention. Preferred compounds of the formula (I) are those in which $R^1$ and $R^2$ independently of one another each represent hydrogen, or represent in each case straight-chain or branched alkyl, alkenyl, alkinyl, cyanoalkyl, hydroxyalkyl, alkoxyalkyl, alkylthioalkyl, alkoxycarbonyl, hydroxycarbonylalkyl, alkoxycarbonylalkyl, aminocarbonylalkyl, alkylaminocarbonylalkyl or dialkylaminocarbonylalkyl with in each case up to 8 carbon atoms in the individual alkyl, or alkenyl, alkinyl or alkoxy parts, or represent oxiranylalkyl which has 1 to 4 carbon atoms in the straight-chain or branched alkyl part and is optionally substituted by alkyl with 1 to 4 carbon atoms, or represent a 5- or 6-membered heterocyclic radical with 1 to 3 identical or different hetero atoms, such as oxygen, sulphur and nitrogen, or represent straight-chain or branched aralkyl which has 1 to 4 carbon atoms in the alkyl part and 6 to 10 carbon atoms in the aryl part and is optionally mono- substituted or polysubstituted by identical or different substituents, or represent aryl which has 6 to 10 carbon atoms and is optionally monosubstituted or polysubstituted by identical or different substituents, possible substituents in the aryl parts in each case being: halogen, cyano, nitro, hydroxyl, in each case straight-chain or branched alkyl, alkoxy, dioxyalkylene, alkylcarbonyloxy and alkylthio with in each case up to 4 carbon atoms, straight-chain or branched halogenoalkyl, halogenogenoalkoxy and halogenoalkylthio with in each case up to 4 carbon atoms and up to 9 identical or different halogen atoms and phenyl, and $R^3$ represents in each case straight-chain or branched halogenoalkyl, halogenoalkenyl or halogenoalkinyl with in each case up to 12 carbon atoms and 1 to 8 identical or different halogen atoms, in particular fluorine, chlorine or bromine, or represents cycloalkyl or cycloalkylalkyl with 3 to 7 carbon atoms in the cycloalkyl part and, where appropriate, 1 to 7 carbon atoms in the straight-chain or branched alkyl part, in each case monosubstituted or polysubstituted by identical or different substituents, possible substituents in each case being: halogen, straight-chain or branched alkyl with 1 to 4 carbon atoms and straight-chain or branched halogenoalkyl with 1 to 4 carbon atoms and 1 to 9 identical or different halogen atoms.

Particularly preferred compounds of the formula (I) are those in which $R^1$ and $R^2$ independently of one another each represent hydrogen, methyl, ethyl, n- or i-propyl, n-, i-, s- or t-butyl, allyl, butenyl, propargyl, cyanomethyl, cyanoethyl, hydroxymethyl, hydroxyethyl, methoxymethyl, methoxyethyl, ethoxymethyl, ethoxyethyl, methylthiomethyl, methoxycarbonyl, ethoxycarbonyl, hydroxycarbonylmethyl, hydroxycarbonylethyl, methoxycarbonylmethyl, methoxycarbonylethyl, ethoxycarbonylmethyl, ethoxycarbonylethyl, aminocarbonylmethyl, methylaminocarbonylmethyl, ethylaminocarbonylmethyl, dimethylaminocarbonylmethyl, diethylaminocarbonylmethyl, aminocarbonylethyl, oxiranylmethyl or oxiranylethyl, or represent 1,1-dioxotetrahydrothien-3-yl, or represent phenyl or benzyl, optionally mono-, di- or trisubstituted by identical or different substituents, possible substituents being: fluorine, chlorine, bromine, iodine, cyano, nitro, hydroxyl, methyl, ethyl, n- and i-propyl, n-, i-, s- and t-butyl, methoxy, ethoxy, dioxymethylene, dioxyethylene, methylthio, ethylthio, acetoxy and propionyloxy, chloromethyl, dichloromethyl, trichloromethyl, trifluoromethyl, dichlorofluoromethyl, chlorodifluoromethyl, trifluoromethoxy, trifluoromethylthio and phenyl, and $R^3$ represents in each case straight-chain or branched halogenoalkyl, halogenoalkenyl or halogenoalkinyl with in each case up to 8 carbon atoms and 1 to 5 identical or different halogen atoms, in particular fluorine or chlorine, or represents cyclopropyl, cyclopentyl, cyclohexyl, cyclopropylmethyl, cyclopen-tylmethyl, cyclohexylmethyl, cyclopropylethyl, 2-cyclopentylethyl or 3-cyclohexyl-n-propyl, in each case mono-, di-, tri-, tetra- or pentasubstituted by identical or different substituents from the group comprising fluorine, chlorine, methyl and/or trifluoromethyl.

Compounds of the formula (I) which may be mentioned in particular are those in which $R^1$ represents hydrogen, methyl, ethyl, n- or i-propyl or n-, i-, s- or t-butyl, $R^2$ represents hydrogen, methyl, ethyl, n- or i-propyl, n-, i-, s- or t-butyl, allyl, butenyl, propargyl, cyanomethyl, cyanoethyl, hydroxymethyl, hydroxyethyl, methoxymethyl, methoxyethyl, ethoxymethyl, ethoxyethyl, methylthiomethyl, methoxycarbonyl, ethoxycarbonyl, hydroxycarbonylmethyl, hydroxycarbonylethyl, methoxycarbonylmethyl, methoxycarbonylethyl, ethoxycarbonylmethyl, ethoxycarbonylethyl, aminocarbonylmethyl, methylaminocarbonylmethyl, ethylaminocarbonylmethyl, dimethylaminocarbonylmethyl, diethylaminocarbonylmethyl, aminocarbonylethyl, oxiranylmethyl or oxiranylethyl, or represents 1,1-dioxotetrahydrothien-3-yl, or represents phenyl or benzyl, optionally mono-, di- or trisubstituted by identical or different substituents, possible substituents being: fluorine, chlorine, bromine, cyano, nitro, hydroxyl, methyl, ethyl, n- and i- propyl, n-, i-, s- and t-butyl, methoxy, ethoxy, dioxymethylene, dioxyethylene, methylthio, ethylthio, acetoxy and propionyloxy, chloromethyl, dichloromethyl, trichloromethyl, trifluoromethyl, dichlorofluoromethyl, chlorodifluoromethyl, trifluoromethoxy, trifluoromethylthio and phenyl, and $R^3$ represents halogenoalkyl or halogenoalkenyl with in each case up to 8 carbon atoms and 1 to 5 identical or different halogen atoms, or $R^1$ and $R^2$ have the abovementioned meanings and $R^3$ represents cyclopropyl or cyclopropylmethyl, in each case mono-, di-, tri-, tetra- or pentasubstituted by identical or different substituents from the group comprising fluorine, chlorine, methyl and trifluoromethyl.

The following substituted pyrazolin-5-ones of the general formula (I) may be mentioned specifically, in addition to the compounds mentioned in the preparation examples:

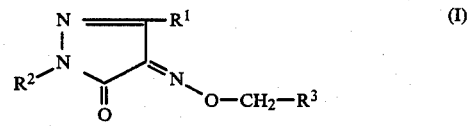

(I)

| $R^1$ | $R^2$ | $R^3$ |
|---|---|---|
| —H | —H | —CH=CCl$_2$ |
| —CH$_3$ | —H | —CH=CCl$_2$ |
| —CH$_3$ | —CH$_3$ | —CH=CCl$_2$ |
| —CH$_3$ | —CH$_2$CN | —CH=CCl$_2$ |
| —H | —CH$_3$ | —CH=CCl$_2$ |
| —H | —CH$_2$CN | —CH=CCl$_2$ |
| —H | —H | —C(Cl)=CHCl |
| —H | —CH$_3$ | —C(Cl)=CHCl |

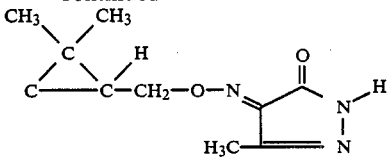

| R¹ | R² | R³ |
|---|---|---|
| —H | —CH₂CN | —C(Cl)=CHCl |
| —CH₃ | —CH₃ | —C(Cl)=CHCl |
| —H | —CH₂CN | —CH=CH—Cl |
| —H | —CH₂—COOC₂H₅ | —CH=CH—Cl |
| —H | —CH₂—CO—NH₂ | —CH=CH—Cl |
| —H | —CH₂—(epoxide CH—CH₂) | —CH=CH—Cl |
| —H | —CH₂—CH₂OH | —CH=CH—Cl |
| —CH₃ | —CH₂—CN | —CH=CHCl |

If, for example, 4-hydroximino-1,3-dimethylpyrazolin-5-one and 2,2-dichlorocyclopropylbromomethane are used as starting substances, the course of the reaction in process (a) according to the invention can be represented by the following equation:

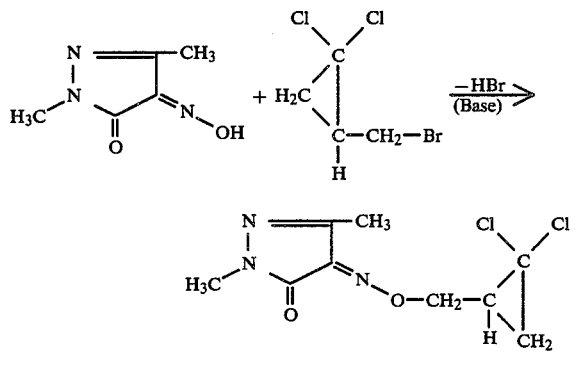

If, for example, ethyl β-keto-α-[(2,2-dimethylcyclopropyl)-methoximino]-butyrate and hydrazine hydrate are used as starting substances, the course of the reaction in process (b) according to the invention can be represented by the following equation:

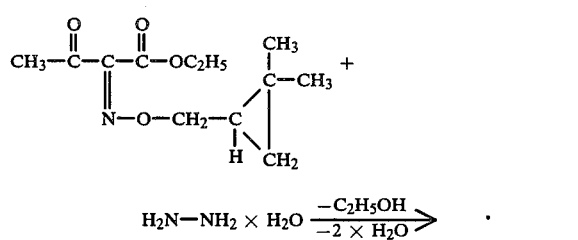

If, for example, 4-[(2,2-dichlorocyclopropyl)methoximino]-3-methyl-pyrazolin-5-one and chloroacetonitrile are used as starting substances, the course of the reaction in process (c) according to the invention can be represented by the following equation:

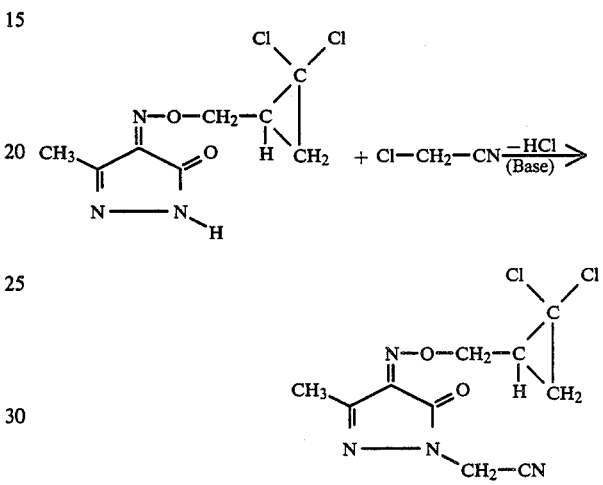

Formula (II) provides a general definition of the 4-oximino-pyrazolin-5-ones required as starting substances for carrying out process (a) according to the invention. In this formula (II), R¹ and R² represent those radicals which have already been mentioned for these substituents in the description of the substances of the formula (I) according to the invention. A preferably represents hydrogen or a sodium or potassium cation.

The 4-oximino-pyrazolin-5-ones of the formula (II) are known in some cases [compare, for example, Ber. dtsch. chem.Ges. 29, 249 (1896); Coll. Czech. Chem. Commun. 25, 55 (1960); Arch. Pharm. 309, 900 (1976); and Liebigs Ann. Chem. 1976, 1380].

They are obtained, for example, by a process in which β-keto esters of the formula (VII)

in which
R¹ has the abovementioned meaning and
R⁴ represents lower alkyl, in particular methyl or ethyl, or in which ethoxymethylenemalonic esters of the formula (VIII)

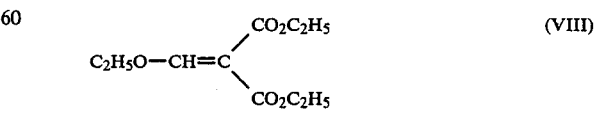

are initially cyclized in a 1st stage with hydrazines of the formula (V)

in which $R^2$ has the meaning given above, if appropriate in the presence of a diluent, such as, for example, ethanol, at temperatures between 0° C. and 100° C., the 4-ethoxycarbonylpyrazolin-5-ones resulting from the malonic ester of the formula (VIII), of the formula (IX)

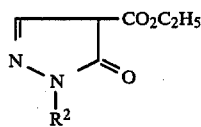 (IX)

in which $R^2$ has the abovementioned meaning, are hydrolyzed and decarboxylated in an intermediate step by customary methods, for example with aqueous hydrochloric acid at temperatures between 50° C. and 120° C., and the pyrazolin-5-ones thus obtainable, of the formula (X)

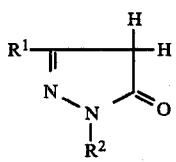 (X)

in which $R^1$ and $R^2$ have the abovementioned meaning, are reacted in a 2nd stage (or 3rd stage) with a nitrosating agent, such as, for example, isopentyl nitrite or sodium nitrite, if appropriate in the presence of a diluent, such as, for example, ethanol, water or aqueous hydrochloric acid, and if appropriate in the presence of a base, such as, for example, sodium methylate, at temperatures between −20° C. and +50° C.

Formula (III) provides a general definition of the alkylating agents required as starting substances for carrying out process (a) according to the invention. In this formula (III), $R^3$ represents those radicals which have already been mentioned for these substituents in connection with the description of the substances of the formula (I) according to the invention. X preferably represents halogen, in particular chlorine, bromine or iodine, or optionally substituted alkylsulphonyloxy, alkoxysulphonyloxy or arylsulphonyloxy, such as, for example, methanesulphonyloxy, methoxysulphonyloxy, trifluoromethanesulphonyloxy or p-toluenesulphonyloxy.

The alkylating agents of the formula (III) are generally known compounds of organic chemistry.

The β-keto esters of the formula (VII) and the ethoxymethylenemalonic ester of the formula (VIII) are likewise generally known.

Formula (IV) provides a general definition of the alkoximinocarboxylic acid esters required as starting substances for carrying out process (b) according to the invention. In this formula (IV), $R^1$ and $R^3$ represent those radicals which have already been mentioned as preferred for these substituents in connection with the description of the substances of the formula (I) according to the invention. R preferably represents straight-chain or branched alkyl with 1 to 4 carbon atoms, in particular methyl or ethyl.

The alkoximinocarboxylic acid esters of the formula (IV) are known in some cases (compare, for example, DE-OS (German Published Specification) No. 2,945,248; DE-OS (German Published Specification) No. 2,810,922; EP-OS (European Published Specification) No. 7,633 or J.Antibiot. 36, 846–854 [1983]).

Compounds which are not yet known are those of the formula (IVa)

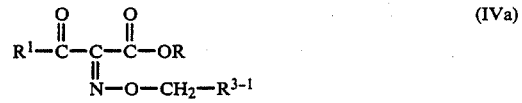 (IVa)

in which
R and $R^1$ have the abovementioned meaning and
$R^{3-1}$ represents halogenoalkenyl or halogenoalkinyl, or represents substituted cycloalkyl, or represents substituted cycloalkylalkyl.

They are obtained by a process analogous to known processes, by a procedure in which hydroximinocarboxylic acid esters of the formula (XI)

 (XI)

in which, R and $R^1$ have the abovementioned meaning, are reacted with alkylating agents of the formula (IIIa)

$R^{3-1}$—$CH_2$—X (III a)

in which
$R^{3-1}$ has the abovementioned meaning and
X represents an electron-withdrawing leaving group, in particular chlorine, bromine or iodine, or represents optionally substituted alkylsulphonyloxy, alkoxysulphonyloxy or arylsulphonyloxy, such as, for example, methanesulphonyloxy, methoxysulphonyloxy, trifluoromethanesulphonyloxy or p-toluenesulphonyloxy,
if appropriate in the presence of a diluent, such as, for example, acetonitrile, and if appropriate in the presence of an acid-binding agent, such as, for example, triethylamine, at temperatures between +10° C. and +80° C.

The alkylating agents of the formula (IIIa) and the hydroximinocarboxylic acid esters of the formula (XI) are generally known compounds of organic chemistry (compare, for example, Helv. Chim. Acta 67, 906–915 [1984]; French patent application No. 2,434,572; Yakugaku Zasshi 87, 1209–1211 [1967] or Chem. Ber. 100, 1245–1247 [1967]).

Formula (Ia) provides a general definition of the 4-alkoximinopyrazolin-5-ones required as starting substances for carrying out process (c) according to the invention. In this formula (Ia), $R^1$ and $R^3$ represent those radicals which have already been mentioned for these substituents in connection with the description of the substances of the formula (I) according to the invention.

The 4-alkoximinopyrazolin-5-ones of the formula (Ia) are compounds according to the invention and are obtainable with the aid of processes (a) or (b) according to the invention.

Formula (VI) provides a general definition of the alkylating agents furthermore required as starting substances for carrying out process (c) according to the invention. In this formula (VI), $R^{2'}$ represents those radicals which have already been mentioned for the substituent $R^2$ in connection with the description of the substances of the formula (I) according to the invention, with the exception of the hydrogen radical and the optionally substituted aryl radicals. Y represents those leaving groups which have already been mentioned for the substituent X in the description of the alkylating agents of the formula (III).

The alkylating agents of the formula (VI) are likewise generally known compounds of organic chemistry.

Possible diluents for carrying out process (a) according to the invention are inert organic solvents or aqueous systems.

These include, in particular, aliphatic-or aromatic, optionally halogenated hydrocarbons, such as, for example, benzine, benzene, toluene, xylene, chlorobenzene, petroleum ether, hexane, cyclohexane, methylene chloride, chloroform or carbon tetrachloride; ethers, such as diethyl ether, dioxane, tetra-hydrofuran or ethylene glycol dimethyl or diethyl ether: ketones, such as acetone or butanone; nitriles, such as acetonitrile or propionitrile, amides, such as dimethylformamide, dimethylacetamide, N-methylformanilide, N-methylpyrrolidone or hexamethylphosphoric acid triamide; esters, such as ethyl acetate; sulphoxides, such as dimethyl sulphoxide, or water or aqueous-organic two-phase mixtures, such as methylene chloride/water or toluene/water.

If appropriate, process (a) according to the invention is carried out in the presence of an acid-binding agent. Possible acid-binding agents are all the customary inorganic or organic bases. These include, for example, alkali metal hydroxides, amides, alcoholates or hydrides, such as sodium hydroxide or potassium hydroxide, sodium methylate or potassium t-butylate, or sodium hydride or sodium amide; alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

The reaction temperature can be varied within a substantial range in carrying out process (a) according to the invention. The reaction is in general carried out at temperatures between $-20°$ C. and $+200°$ C., preferably at temperatures between $0°$ C. and $+150°$ C.

In carrying out process (a) according to the invention, in general 1.0 to 3.0 moles, preferably 1.0 to 1.5 moles, of alkylating agent of the formula (III) and, if appropriate, 1.0 to 3.0 moles, preferably 1.0 to 1.5 moles, of acid-binding agent are employed per mole of 4-oximino-pyrazolin-5-one of the formula (II).

If an organic-aqueous two-phase system is used, the reaction can be carried out, if appropriate, in the presence of 0.1 to 1 mole of a suitable phase transfer catalyst, such as, for example, a quaternary ammonium or phosphonium compound. Triethylbenzylammonium chloride and benzyl-dodecyl-dimethylammonium chloride may be mentioned as examples.

The reaction products of the formula (I) are worked up and isolated by customary methods.

Possible diluents for carrying out process (b) according to the invention are likewise inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform or carbon tetrachloride; ethers, such as diethyl ether, dioxane, tetrahydrofuran or ethylene glycol dimethyl or diethyl ether, or alcohols, such as methanol, ethanol or propanol.

The reaction temperatures can be varied within a substantial range in carrying out process (b) according to the invention. The reaction is in general carried out at temperatures between $0°$ C. and $150°$ C., preferably at temperatures between $20°$ C. and $120°$ C.

For carrying out process (b) according to the invention, in general 0.8 to 2.5 moles, preferably 1.0 to 1.2 moles, of hydrazine derivative of the formula (V) are employed per mole of alkoximinocarboxylic acid ester of the formula (IV). The reaction is carried out and the reaction products of the formula (I) are worked up and isolated by customary methods.

Possible diluents for carrying out process (c) according to the invention are likewise inert organic solvents. The organic solvents or aqueous-organic two-phase mixtures mentioned for process (a) are preferably used.

If appropriate, process (c) according to the invention is carried out in the presence of an acid-binding agent. The inorganic or organic bases mentioned for process (a) are preferably used as acid-binding agents.

The reaction temperatures can likewise be varied within a substantial range in carrying out process (c) according to the invention. The reaction is in general carried out at temperatures between $-20°$ C. and $+200°$ C., preferably at temperatures between $0°$ C. and $+150°$ C.

In carrying out process (c) according to the invention, in general 1.0 to 3.0 moles, preferably 1.0 to 1.5 moles, of alkylating agent of the formula (VI) and, if appropriate, 0.5 to 3.0 moles, preferably 0.6 to 1.5 moles, of acid-binding agent are employed per mole of 4-alkoximino-pyrazolin-5-one of the formula (Ia).

The reaction is carried out and the reaction products of the formula (I) are worked up and isolated by generally customary processes.

The active compounds according to the invention have a powerful biological action and can be employed in practice for combating undesirable pests. The active compounds are suitable for use as agents for combating pests, above all as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can be used here with particularly good success for combating cereal diseases, such as, for example, the glume blotch of wheat causative organism *Leptosphaeria nodorum*), against the stripe disease of barley causative organism (*Drechslera graminea*), against loose smut disease and against Fusarium species, for combating vegetable diseases, such as, for example, against the brown rot of tomato causative organism (*Phytophthora infestans*) or for combating rice diseases, such as, for example, against the rice spot disease causative organism (*Pyricularia oryzae*). In addition to protective activity, the active compounds according to the invention also exhibit systemic properties and can therefore also be used with good success as seed dressing agents, for example against the powdery mildew of cereal causative organism (*Erysiphe graminis*).

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom by further dilution, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

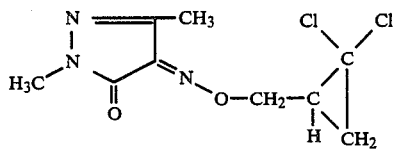

(Process a)

4.9 ml (0.035 mole) of triethylamine are added to 4.64 g (0.033 mole) of 1,3-dimethyl-4-hydroximino-pyrazolin-5-one and 6.71 g (0.033 mole) of 2,2-dichlorocyclopropyl-bromomethane in 80 ml of acetonitrile at room temperature and the mixture is subsequently stirred for 18 hours. For working up, the solvent is removed in vacuo, the residue is taken up in methylene chloride, the mixture is washed with water and dried over sodium sulphate, the solvent is removed in vacuo and the residue is purified by chromatography on silica gel (mobile phase=methylene chloride/ether; 10:1).

2.7 g (31% of theory) of 4-[(2,2-dichlorocyclopropyl)-methoximino]-1,3-dimethyl-pyrazolin-5-one are obtained as an oil.

$^1$H-NMR (CDCl$_3$): δ=4.3–4.8 ppm.

Preparation of the starting compound

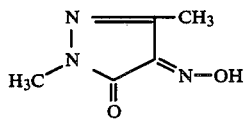

183 g (1.56 moles) of isopentyl nitrite are added dropwise to 175 g (1.56 moles) of 1,3-dimethyl-pyrazolin-5-one and 84.4 g (1.56 moles) of sodium methylate in 1 / of absolute ethanol, while stirring and cooling with ice, so that the internal temperature does not exceed 25° C. to 30° C. When the addition has ended, the mixture is stirred at room temperature for a further 24 hours and the sodium salt of 1,3-dimethyl-4-hydroximino-pyrazolin-5-one which has precipitated is filtered off with suction. The crystalline product is dissolved in 1 / of water and acidified with glacial acetic acid. To bring the precipitation to completion, the mixture is cooled at 0° C. for several hours and the product is then filtered off with suction.

162 g (74% of theory) of 1,3-dimethyl-4-hydroximino-pyrazolin-5-one of melting point 93° C. are obtained.

Example 2

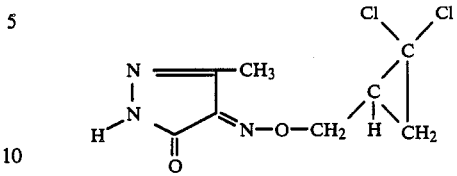

(Process b)

14 ml (0.1 mole) of triethylamine are added to 11.43 g (0.09 mole of 3-methyl-4-hydroximino-pyrazolin-5-one and 18.36 g (0.09 mole) of 2,2-dichlorocyclopropyl-bromomethane in 100 ml of acetonitrile at room temperature and the mixture is subsequently stirred for 18 hours. For working up, the solvent is removed in vacuo, the residue is taken up in methylene chloride, the mixture is washed with water and dried over sodium sulphate, the solvent is removed in vacuo and the residue is purified by chromatography on silica gel (mobile phase=methylene chloride/ether; 10:1). 8.4 g (37% of theory) of 4-[(2,2-dichlorocyclopropyl)-methoximino]-3-methyl-pyrazolin-5-one are obtained as an oil.

$^1$H-NMR (CDCl$_3$): δ=4.33–4.8 ppm.

Example 3

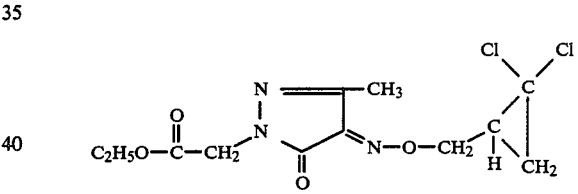

(Process c)

3.3 g (0.013 mole) of 4-[(2,2-dichloro-cyclopropyl)-methoximino]-3-methyl-(1H)-pyrazolin-5-one and 2.5 g (0.015 mole) of ethyl bromoacetate are heated under reflux together with 1.4 g (0.01 mole) of potassium carbonate in 50 ml of acetone for 18 hours. For working up, the solvent is removed in vacuo, the residue is taken up in methylene chloride, the mixture is washed with water and dried over sodium sulphate, the solvent is removed in vacuo and the residue is purified by chromatography on silica gel (mobile phase=methylene chloride/ether; 10:1). 3.7 g (83% of theory) of 4-[(2,2-dichlorocyclopropyl)-methoximino]-1-ethoxycarbonylmethyl-3-methyl-pyrazolin-5-one are obtained as an oil.

$^1$H-NMR (CDCl$_3$): δ=5.27 ppm.

The substituted pyrazolin-5-ones of the general formula (I) are obtained in a corresponding manner and in accordance with the general statements on the preparation:

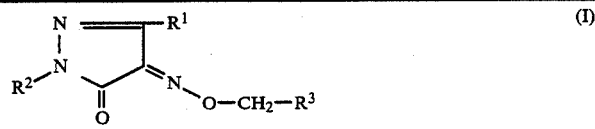

(I)

| Example No. | R¹ | R² | R³ | ¹H—NMR*) |
|---|---|---|---|---|
| 4 | CH₃ | CH₃ | ![structure: cyclopropane with CCl₂, C(CH₃)₂, CH] | 4.47–4.67 |
| 5 | H | CH₃ | ![structure: cyclopropane with CCl₂, CH₂, CH] | 4.4–4.8 |
| 6 | H | CH₃ | ![structure: cyclopropane with CCl₂, C(CH₃)₂, CH] | 4.35–4.75 |
| 7 | CH₃ | H | ![structure: cyclopropane with CCl₂, C(CH₃)₂, CH] | 4.5–4.7 |
| 8 | CH₃ | NC—CH₂— | ![structure: cyclopropane with CCl₂, CH₂, CH] | 4.4–4.85 |
| 9 | CH₃ | NC—CH₂— | ![structure: cyclopropane with CCl₂, C(CH₃)₂, CH] | 4.5–4.75 |
| 10 | CH₃ | C₂H₅OCO—CH₂— | ![structure: cyclopropane with CCl₂, C(CH₃)₂, CH] | 4.1–4.35 |
| 11 | H | NC—CH₂CH₂— | ![structure: cyclopropane with CCl₂, CH₂, CH] | 4.5–4.8 |
| 12 | H | NC—CH₂CH₂— | ![structure: cyclopropane with CCl₂, C(CH₃)₂, CH] | 4.35–4.8 |
| 13 | CH₃ | HO—CH₂CH₂— | ![structure: cyclopropane with CCl₂, CH₂, CH] | 4.35–48 |

-continued $$\underset{R^2}{\overset{N=\!\!=}{\underset{|}{N}}}\underset{\underset{O}{\parallel}}{\overset{}{C}}\!=\!\!N\!-\!O\!-\!CH_2\!-\!R^3 \quad (I)$$
(with R¹ on the =CH carbon)

| Example No. | R¹ | R² | R³ | ¹H—NMR*) |
|---|---|---|---|---|
| 14 | CH₃ | HO—CH₂CH₂— | 2,2-dichloro-3,3-dimethylcyclopropyl (Cl,Cl on C; CH₃,CH₃ on C; H on C) | 4.47–4.8 |
| 15 | CH₃ | NC—CH₂CH₂— | 2,2-dichlorocyclopropyl (Cl,Cl on C; H₂C; CH—H) | 4.35–4.83 |
| 16 | CH₃ | NC—CH₂CH₂— | 2,2-dichloro-3,3-dimethylcyclopropyl (Cl,Cl; CH₃,CH₃; H) | 4.5–4.68 |
| 17 | CH₃ | CH₃ | Cl—CH=CH— | 4.87–4.99 |
| 18 | H | CH₃ | Cl—CH=CH— | 4.92–4.95 |
| 19 | H | CH₃ | Cl—CH=CH— | 4.92–4.98 (isomer mixture) |
| 20 | H | H | 2,2-dichlorocyclopropyl (Cl,Cl; H₂C; CH—H) | 4.4–4.85 |
| 21 | H | H | 2,2-dichlorocyclopropyl (Cl,Cl; H₂C; CH—H) | 4.42–4.8 |
| 22 | H | H | Cl—CH=CH— | 4.87–4.93 |
| 23 | H | NC—CH₂CH₂— | Cl—CH=CH— | 4.88–4.95 |
| 24 | CH₃ | NC—CH₂CH₂— | Cl—CH=CH— | 4.92–5.0 |
| 25 | H | CH₃ | 2,2-dichloro-3-methylcyclopropyl (Cl,Cl; H₂C; C—CH₃) | 4.6–4.8 |
| 26 | CH₃ | CH₃ | $Cl_2C\!=\!CH\!-\!C(CH_3)_2\!-\!CH_2\!-$ | 4.43–4.6 |
| 27 | H | CH₃ | $Cl_2C\!=\!CH\!-\!C(CH_3)_2\!-\!CH_2\!-$ | 4.45–4.6 |
| 28 | H | CH₃ | $Cl\!-\!C(CH_3)_2\!-\!CH_2\!-$ | 4.73–4.83 |

-continued $$\begin{array}{c} N \stackrel{}{=\!=\!=} R^1 \\ R^2 - N \\ \phantom{R^2-}| \\ \phantom{R^2-N}O \phantom{xxx} N-O-CH_2-R^3 \end{array} \quad (I)$$

| Example No. | R¹ | R² | R³ | ¹H—NMR*) |
|---|---|---|---|---|
| 29 | CH₃ | CH₃ | Cl–C(CH₃)(CH₃)–CH₂– | 4.7–4.8 |
| 30 | CH₃ | CH₃ | cyclopropane with CCl₂, C(CH₃)₂, CH(–CH₂–) | 4.53–4.67 |
| 31 | H | CH₃ | cyclopropane with CCl₂, C(CH₃)₂, CH(–CH₂–) | 4.52–4.67 |
| 32 | CH₃ | C₂H₅ | cyclopropane with CCl₂, CH₂, CH– | 4.33–4.8 |
| 33 | CH₃ | CH₃–(CH₂)₂– | cyclopropane with CCl₂, CH₂, CH– | 4.38–4.8 |
| 34 | CH₃ | CH₃–(CH₂)₃– | cyclopropane with CCl₂, CH₂, CH– | 4.38–4.8 |
| 35 | CH₃ | (CH₃)₂CH– | cyclopropane with CCl₂, CH₂, CH– | 4.38–4.8 |
| 36 | CH₃ | H₂C(–O–)CH–CH₂– (oxirane) | cyclopropane with CCl₂, CH₂, CH– | 4.33–4.82 |
| 37 | H | HO–CH₂–CH₂ | cyclopropane with CCl₂, CH₂, CH– | 4.4–4.8 |

*) The ¹H-NMR spectra were recorded in CDCL₃ with tetramethylsilane as the internal standard. As a rule the chemical shifts as δ values for the grouping >C=N—O—CH₂— are quoted.

USE EXAMPLES

The compound shown below was employed as the comparison substance in the following use examples:

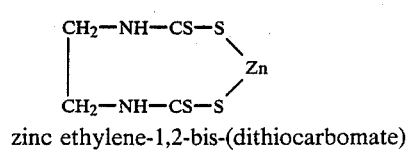

(A)

zinc ethylene-1,2-bis-(dithiocarbomate)

Example A

Phytophthora Test (tomato)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabin at 100% relative atmospheric humidity and at about 20° C.

Evaluation is carried out 3 days after the inoculation.

In this test, a clearly superior activity compared with the prior art is shown, for example, by the compounds according to preparation Examples 1, 5, 9, 16, 21 and 22.

Example B

*Leptosphaeria nodorum* test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to preparation Examples 1, 2, 3, 4, 6, 7, 8, 9 and 10.

Example C

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to preparation Examples 7, 8, 9, 12, 14, 16 and 21.

It will be understood that the specification and examples are illustrative but not limitative of the present invention and that other embodiments within the spirit and scope of the invention will suggest themselves to those skilled in the art.

We claim:

1. A substituted pyrazolin-5-one of the formula

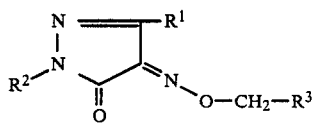

in which

R$^1$ and R$^2$ independently of one another each represents hydrogen, or represent in each case straight-chain or branched alkyl, alkenyl, alkinyl, cyanoalkyl, hydroxyalkyl, alkoxyalkyl, alkylthioalkyl, alkoxycarbonyl, hydroxycarbonylalkyl, alkoxycarbonylalkyl, aminocarbonylalkyl, alkylaminocarbonylalkyl or dialkylaminocarbonylalkyl with in each case up to 8 carbon atoms in the individual alkyl, or alkenyl, alkinyl or alkoxy parts, or represents oxiranylalkyl which has 1 to 4 carbon atoms in the straight-chain or branched alkyl part and is optionally substituted by alkyl with 1 to 4 carbon atoms, or represents a 1,1-dioxotetrahydrothien-3-yl, or represents aralkyl which has 1 to 4 carbon atoms in the straight-chain or branched alkyl part and 6 to 10 carbon atoms in the aryl part and is optionally monosubstituted or polysubstituted by identical or different substituents, or represents aryl which has 6 to 10 carbon atoms and is optionally substituted, the optional substituents on the various aryl parts being independently selected from the group consisting of halogen, cyano, nitro, hydroxyl, in each case straight-chain or branched alkyl, alkoxy, dioxyalkylene, alkylcarbonyloxy and alkylthio with in each case up to 4 carbon atoms, straight-chain or branched halogenoalkyl, halogenoalkoxy and halogenoalkylthio with in each case up to 4 carbon atoms and up to 9 identical or different halogen atoms and phenyl, and R$^3$ represents in each case straight-chain or branched halogenoalkyl, halogenoalkenyl or halogenoalkinyl with in each case up to 12 carbon atoms and 1 to 8 identical or different halogen atoms, or represents cycloalkyl or cycloalkylalkyl with 3 to 7 carbon atoms in the cycloalkyl part and, where appropriate, 1 to 7 carbon atoms in the straight-chain or branched alkyl part, in each case substituted by substituents. independently selected from the group consisting of halogen, straight-chain or branched alkyl with 1 to 4 carbon atoms and straight-chain or branched halogenoalkyl with 1 to 4 carbon atoms and 1 to 9 identical or different halogen atoms.

2. A substituted pyrazolin-5-one according to claim 1, in which $R^1$ and $R^2$ independently of one another each represents hydrogen, methyl, ethyl, n- or i-propyl, n-, i-, s- or t-butyl, allyl, butenyl, propargyl, cyanomethyl, cyanoethyl, hydroxymethyl, hydroxyethyl, methoxymethyl, methoxyethyl, ethoxymethyl, ethoxyethyl, methylthiomethyl, methoxycarbonyl, ethoxycarbonyl, hydroxycarbonyl, hydroxycarbonylethyl, methoxycarbonylmethyl, methoxycarbonylethyl, ethoxycarbonylmethyl, ethoxycarbonylethyl, aminocarbonylmethyl, methylaminocarbonylmethyl, ethylaminocarbonylmethyl, dimethylaminocarbonylmethyl, diethylaminocarbonylmethyl, aminocarbonylethyl, oxiranylmethyl or oxiranylethyl, or represent 1,1-dioxotetrahydrothien-3-yl, or represents phenyl or benzyl, optionally mono-, di-or trisubstituted by substituents independently selected from the group consisting of fluorine, chlorine, bromine, iodine, cyano, nitro, hydroxyl, methyl, ethyl, n- and i-propyl, n-, i-, s- and t-butyl, methoxy, ethoxy, dioxymethylene, dioxyethylene, methylthio, ethylthio, acetoxy and propionyloxy, chloromethyl, dichloromethyl, trichloromethyl, trifluoromethyl, dichlorofluoromethyl, chlorodifluoromethyl, trifluoromethoxy, trifluoromethylthio and phenyl, and $R^3$ represents in each case straight-chain or branched halogenoalkyl, halogenoalkenyl or halogenoalkinyl with in each case up to 8 carbon atoms and 1 to 5 identical or different halogen atoms, or represents cyclopropyl, cyclopentyl, cyclohexyl, cyclopropylmethyl, cyclopentylmethyl, cyclohexylmethyl, cyclopropylethyl, 2-cyclopentylethyl or 3-cyclohexyl-n-propyl, in each case mono-, di-, tri-, tetra- or pentasubstituted by substituents independently selected from the group consisting of fluorine, chlorine, methyl and/or trifluoromethyl.

3. A substituted pyrazolin-5-one according to claim 1, in which $R^1$ represents hydrogen, methyl, ethyl, n- or i-propyl or n-, i-, s- or t-butyl, $R^2$ represents hydrogen, methyl, ethyl, n- or i-propyl, n-, i-, s- or t-butyl, allyl, butenyl, propargyl, cyanomethyl, cyanoethyl, hydroxymethyl, hydroxyethyl, methoxymethyl, methoxyethyl, ethoxymethyl, ethoxyethyl, methylthiomethyl, methoxycarbonyl, ethoxycarbonyl, hydroxycarbonylmethyl, hydroxycarbonylethyl, methoxycarbonylmethyl, methoxycarbonylethyl, ethoxycarbonylmethyl, ethoxycarbonylethyl, aminocarbonylmethyl, methylaminocarbonylmethyl, ethylaminocarbonylmethyl, dimethylaminocarbonylmethyl, diethylaminocarbonylmethyl, aminocarbonylethyl, oxiranylmethyl or oxiranylethyl, or represents 1,1-dioxotetrahydrothien-3-yl, or represents phenyl or benzyl, optionally mono-, df- or trisubstituted by substituents independently selected from the group consisting of fluorine, chlorine, bromine, iodine, cyano, nitro, hydroxyl, methyl, ethyl, n- and i-propyl, n-, i-, s- and t-butyl, methoxy, ethoxy, dioxymethylene, dioxyethylene, methylthio, ethylthio, acetoxy and propionyloxy, chloromethyl, dichloromethyl, trichloromethyl, trifluoromethyl, dichlorofluoromethyl, chlorodifluoromethyl, trifluoromethoxy, trifluoromethylthio and phenyl, and $R^3$ represents halogenoalkyl or halogenoalkenyl with in each case up to 8 carbon atoms and 1 to 5 identical or different halogen atoms.

4. A substituted pyrazolin-5-one according to claim 1 in which $R^1$ represents hydrogen, methyl, ethyl, n- or i-propyl or n-, i-, s- or t-butyl, $R^2$ represents hydrogen, methyl, ethyl, n- or i-propyl, n-, i-, s- or t-butyl, allyl, butenyl, propargyl, cyanomethyl, cyanoethyl, hydroxymethyl, hydroxyethyl, methoxymethyl, methoxyethyl, ethoxymethyl, ethoxyethyl, methylthiomethyl, methoxycarbonyl, ethoxycarbonyl, hydroxycarbonylmethyl, hydroxycarbonylethyl, methoxycarbonylmethyl, methoxycarbonylethyl, ethoxycarbonylmethyl, ethoxycarbonylethyl, aminocarbonylmethyl, methylaminocarbonylmethyl, ethylaminocarbonylmethyl, dimethylaminocarbonylmethyl, diethylaminocarbonylmethyl, aminocarbonylethyl, oxiranylmethyl or oxiranylethyl, or represents 1,1-dioxotetrahydrothien-3-yl, or represents phenyl or benzyl, optionally mono-, di- or trisubstituted by substituents independently selected from the group consisting of fluorine, chlorine, bromine, iodine, cyano, nitro, hydroxyl, methyl, ethyl, n-and i-propyl, n-, i-, s- and t-butyl, methoxy, ethoxy, dioxymethylene, dioxyethylene, methylthio, ethylthio, acetoxy and propionyloxy, chloromethyl, dichloromethyl, trichloromethyl, trifluoromethyl, dichlorofluoromethyl, chlorodifluoromethyl, trifluoromethoxy, trifluoromethylthio and phenyl, and $R^3$ represents cyclopropyl or cyclopropylmethyl, in each case mono-, di-, tri-, tetra- or penta- substituted by identical or different substituents selected from the group consisting of fluorine, chlorine, methyl and trifluoromethyl.

5. A compound according to claim 1, wherein such compound is 4-[(2,2-dichloro-3,3-dimethyl-cyclopropyl)methoximino]-1,3-dimethyl-pyrazolin-5-one of the formula

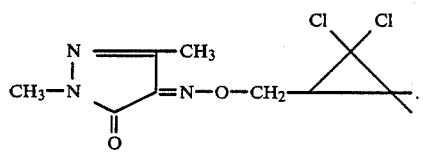

6. A compound according to claim 2, wherein such compound is 4-[(2,2-dichloro-3,3-dimethyl-cyclopropyl) methoximino]-3-methyl-pyrazolin-5-one of the formula

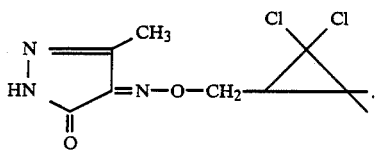

7. A compound according to claim 2, wherein such compound is 4-[(2,2-dichloro-3,3-dimethyl-cyclopropyl) methoximino]-1-cyanomethyl-3-methyl-pyrazolin-5-one of the formula

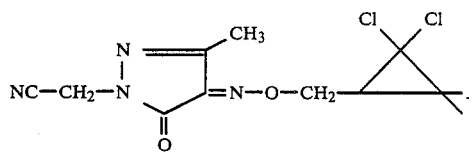

8. A compound according to claim 2, wherein such compound is 4-[(2,2-dichloro-3,3-dimethyl-cyclpropyl) methoximino]-1-cyanoethyl-pyrazolin-5-one of the formula

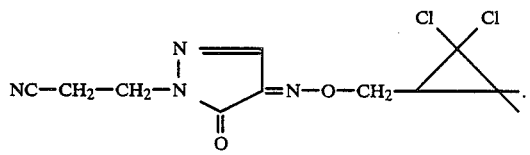

9. A compound according to claim 1, wherein such compound is 4-[(2,2-dichloro-cyclopropyl)-methoximino]-1hydroxyethyl-3-methyl-pyrazolin-5-one of the formula

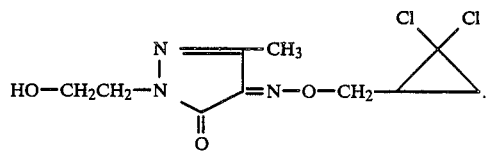

10. A compound according to claim 1, wherein such compound is 4-[(2,2-dichloro-3,3-dimethyl-cyclopropyl)methoximino]-1-hydroxyethyl-3-methyl-pyrazolin-5-one of the formula

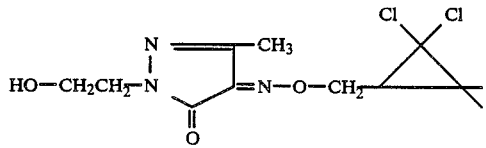

11. A compound according to claim 1, wherein such compound is 4-[(2,2-dichloro-3,3-dimethyl -cyclopropyl)methoximino]-1-cyanoethyl-3-methyl-pyrazolin-5-one of the formula

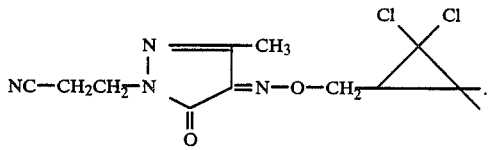

12. A compound according to claim 1, wherein such compound is 4-(3-chloroallyloximino)-1,3-dimethyl-pyrazolin-5-one of the formula

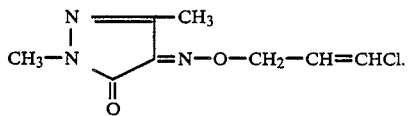

13. A compound according to claim 1, wherein such compound is 4-(3-chloroallyloximino)-1-methylpyrazolin-5-one of the formula

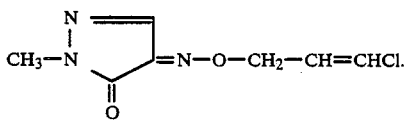

14. A compound according to claim 1, wherein such compound is 4-[(2,2-dichloro-cyclopropyl)-methoximino]pyrazolin-5-one of the formula

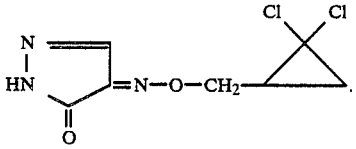

15. A fungicidal composition comprising a fungicidally effective amount of a compound according to claim 1 in admixture with a diluent.

16. A method of combating fungi which comprises applying to such fungi or to a fungus habitat a fungicidally effective amount of a compound according to claim 1.

17. The method according to claim 16, wherein such compound is
4-[(2,2-dichloro-3,3-dimethyl-cyclopropyl)methoximino]-1,3-dimethyl-pyrazolin-5-one,
4-[(2,2-dichloro-3,3-dimethyl-cyclopropyl)methoximino]-3-methyl-pyrazolin-5-one,
4-[(2,2-dichloro-3,3-dimethyl-cyclopropyl)methoximino]-1-cyanomethyl-3-methyl-pyrazolin 5-one,
4-[(2,2-dichloro-3,3-dimethyl-cyclopropyl)methoximino]-1-cyanoethyl-pyrazolin-5-one,
4-[(2,2-dichloro-cyclopropyl)-methoximino]1-hydroxyethyl-3-methyl-pyrazolin-5-one,
4-[(2,2-dichloro-3,3-dimethyl-cyclopropyl)methoximino]-1-hydroxyethyl-3-methyl-pyrazolin-5-one,
4-[(2,2-dichloro-3,3-dimethyl-cyclopropyl)methoximino]-1-cyanoethyl-3-methyl-pyrazolin-5-one,
4-(3-chloroallyloximino-1,3-dimethyl-pyrazolin-5-one,
4-(3-chloroallyloximino)-1-methyl-pyrazolin-5-one or
4-[(2,2-dichloro-cyclopropyl)-methoximino]pyrazolin-5-one.

* * * * *